United States Patent [19]
Miller et al.

[11] Patent Number: 6,069,153
[45] Date of Patent: *May 30, 2000

[54] INDENOINDOLES AND BENZOCARBAZOLES AS ESTROGENIC AGENTS

[75] Inventors: Chris P. Miller, Strafford; Michael D. Collini, Clifton Heights, both of Pa.; Bach D. Tran, Baltimore, Md.

[73] Assignee: American Home Products Corporation, Madison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/306,072

[22] Filed: May 6, 1999

Related U.S. Application Data
[60] Provisional application No. 60/100,428, May 12, 1998.

[51] Int. Cl.[7] .................. A61K 31/445; A61K 31/40; A61K 31/55; C07D 401/12; C07D 403/12
[52] U.S. Cl. .................. 514/323; 546/200; 548/420; 540/602; 514/212; 514/410
[58] Field of Search .................. 546/200; 548/420; 514/323

[56] References Cited

U.S. PATENT DOCUMENTS

| | | | |
|---|---|---|---|
| 4,656,187 | 4/1987 | Black et al. | 514/422 |
| 4,894,373 | 1/1990 | Young | 514/239.2 |
| 4,943,572 | 7/1990 | von Angerer | 514/235.2 |
| 5,023,254 | 6/1991 | von Angerer | 514/235.5 |
| 5,051,442 | 9/1991 | Salituro et al. | 514/419 |

(List continued on next page.)

FOREIGN PATENT DOCUMENTS

| | | |
|---|---|---|
| 0166591 | 1/1986 | European Pat. Off. . |
| 0242167 | 10/1987 | European Pat. Off. . |
| 0509762 | 10/1992 | European Pat. Off. . |
| 0510398 | 10/1992 | European Pat. Off. . |
| 0639567 | 2/1995 | European Pat. Off. . |
| 94027576 | 5/1996 | Russian Federation . |
| 511841 | 8/1971 | Switzerland . |
| 219596 | 10/1968 | U.S.S.R. . |
| 1123263 | 8/1968 | United Kingdom . |
| 1168450 | 10/1969 | United Kingdom . |
| 1566307 | 4/1980 | United Kingdom . |
| 9113060 | 9/1991 | WIPO . |
| 9310741 | 6/1993 | WIPO . |
| 9323374 | 11/1993 | WIPO . |
| 9517383 | 6/1995 | WIPO . |
| 9522524 | 8/1995 | WIPO . |
| 9603375 | 2/1996 | WIPO . |

OTHER PUBLICATIONS von Angerer et al., J. Med. Chem.., vol. 33, No. 9, pp. 2635–2640, 1990.
von Angerer et al., J. Med. Chem., vol. 30, No. 1., pp. 131–136, 1987.
Rackeley, Contemporary Treatment in Cardiovascular Disease, 1, pp. 49–58 (1996).
von Angerer et al., Ann. N.Y. Aca. Sci., pp. 176, 177, 189, 1995.
Oparil "Hypertension in postmenopausal Women:Pathology and Management" EMBASE 95:283951, 1995.
von Angerer et al., J. Med. Chem. vol. 27, pp. 1439–1447, 1984.
Biberger, J. Steroid Biochem. Molec., vol. 58, No. 1, pp. 31–43 (1996).
Evans et al., Bone, vol. 17, No. 4, Oct. 1995, 181S–190S.
Von Angerer, J. Med. Chem. (1983), vol. 26 (1), pp. 113–116.
Kauppila et al., Am. J. Obstet. Gynecol., vol. 140, No. 7, 1981, pp. 787–792.
Kauppila et al., Arch. Gynecol. (1983) 234:49–58.
Segall et al., Eur. J. Med. Chem., 30, No. 2, 165–169 (1995).
Klinicheskaya Farmakologiya i Terapiya, 1996, 5 (1), pp. 70–75.
Klinicheskaya Farmakologiya i Terapiya, 1994, 3 (3), pp. 30–39.

*Primary Examiner*—Laura L. Stockton
*Attorney, Agent, or Firm*—Steven R. Eck

[57] ABSTRACT

The present invention relates to new substituted benzo[a] carbozoles and indenoindoles which are useful as estrogenic agents, as well as pharmaceutical compositions and methods of treatment utilizing these compounds, having the general structures below.

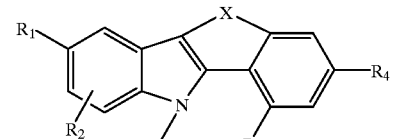

or

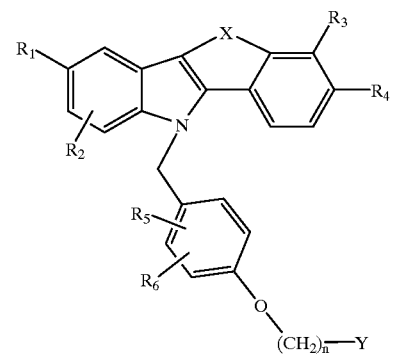

14 Claims, No Drawings

U.S. PATENT DOCUMENTS

| | | | |
|---|---|---|---|
| 5,124,335 | 6/1992 | Patchett et al. | 514/300 |
| 5,185,360 | 2/1993 | Sainsbury et al. | 514/410 |
| 5,389,641 | 2/1995 | Naka et al. | 514/303 |
| 5,395,842 | 3/1995 | Labrie et al. | 514/320 |
| 5,496,844 | 3/1996 | Inai et al. | 514/415 |
| 5,534,527 | 7/1996 | Black et al. | 514/333 |
| 5,550,107 | 8/1996 | Labrie | 514/11 |
| 5,552,401 | 9/1996 | Cullinan et al. | 514/233.5 |
| 5,591,753 | 1/1997 | Black et al. | 514/324 |
| 5,646,137 | 7/1997 | Black et al. | 514/171 |
| 5,672,609 | 9/1997 | Bryant et al. | 514/318 |
| 5,852,039 | 12/1998 | Sohda et al. | 514/311 |

INDENOINDOLES AND BENZOCARBAZOLES AS ESTROGENIC AGENTS

This application claims the benefit of U.S. Provisional application No. 60/100,428 filed May 12, 1998, which was converted from U.S. patent application Ser. No. 09/076,407, filed May 12, 1998, pursuant to a petition filed under 37 C.F.R. 1.53(c)(2)(i).

The present invention relates to new indenoindole and benzocarbazole compounds which are useful as estrogenic agents, as well as pharmaceutical compositions and methods of treatment utilizing these compounds.

BACKGROUND OF THE INVENTION

The use of hormone replacement therapy for bone loss prevention in post-menopausal women is well precedented. The normal protocol calls for estrogen supplemention using such formulations containing estrone, estriol, ethynyl estradiol or conjugated estrogens isolated from natural sources (i.e. Premarin® conjugated estrogens from Wyeth-Ayerst). In some patients, therapy may be contraindicated due to the proliferative effects of unopposed estrogens (estrogens not given in combination with progestins) have on uterine tissue. This proliferation is associated with increased risk for endometriosis and/or endometrial cancer. The effects of unopposed estrogens on breast tissue is less clear, but is of some concern. The need for estrogens which can maintain the bone sparing effect while minimizing the proliferative effects in the uterus and breast is evident. Certain nonsteroidal antistrogens have been shown to maintain bone mass in the ovariectomized rat model as well as in human clinical trials. Tamoxifen (sold as Novadex® brand tamoxifen citrate by Zeneca Pharmaceuticals, Wilmington, Del.), for example, is a useful palliative for the treatment of breast cancer and has been demonstrated to exert an estrogen agonist-like effect on the bone, in humans. However, it is also a partial agonist in the uterus and this is cause for some concern. Raloxifene, a benzothiophene antiestrogen, has been shown to stimulate uterine growth in the ovariectomized rat to a lesser extent than Tamoxifen while maintaining the ability to spare bone. A suitable review of tissue selective estrogens is seen in the article "Tissue-Selective Actions of Estrogen Analogs", *Bone* Vol. 17, No. 4, October 1995, 181S–190S.

Indenoindoles and benzocarbazoles, as shown in figures I and II, have not been reported for compounds of the type described bearing the side chain from the nitrogen of the indole as described in the present invention. See Ger. Offen., DE 3821148 A1 891228 and WO 96/03375 describes indenoindoles and benzocarbazoles which do not bear or claim the basic side chains of this invention. Also see Segall, et al, *Eur.J.Med.Chem.,* 30 no #2 165–169 (1995) for benzocarbazoles with estrogenic/antiestrogenic activity.

DESCRIPTION OF THE INVENTION

Indenoindoles and benzo[a]carbazoles of the general structure type shown in figures (I) and (II) are estrogen agonists/antagonists useful for the treatment of diseases associated with estrogen deficiency. The compounds of the present invention show strong binding to the estrogen receptor, and are capable of antagonizing the effects of 17β-estradiol (in an infection luciferase assay) while showing little intrinsic estrogenic agonist activity when dosed alone.

The present invention includes compounds of the formulas in Figures I or II, below:

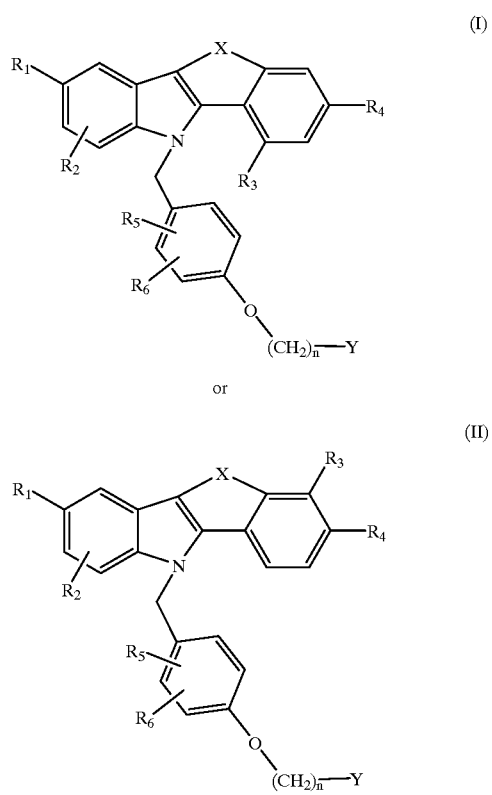

wherein:
$R_1$ is selected from H, OH or the $C_1$–$C_{12}$ esters (straight chain or branched) or $C_1$–$C_{12}$ (straight chain or branched or cyclic) alkyl ethers thereof, or halogens; or halogenated ethers including trifluoromethyl and trichloromethyl ethers;
$R_2$, $R_3$, $R_4$, $R_5$, and $R_6$ are independently selected from H, OH or the $C_1$–$C_{12}$ esters (straight chain or branched) or $C_1$–$C_{12}$ alkyl ethers (straight chain or branched or cyclic) thereof, halogens, or halogenated ethers including trifluoromethyl ester and trichloromethyl ether, cyano, $C_1$–$C_6$ alkyl (straight chain or branched), or trifluoromethyl, with the proviso that, when $R_1$ is H, $R_2$ is not OH;
X is $(CH_2)_{n'}$ or —CH=CH—;
n' is 1 or 2
n is 2 through 4;
Y is selected from:
a) the moiety:

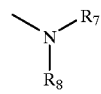

wherein $R_7$ and $R_8$ are independently selected from the group of H, $C_1$–$C_6$ alkyl, or phenyl.
b) a five-membered saturated, unsaturated or partially unsaturated heterocycle containing up to two heteroatoms selected from the group consisting of —O—, —NH—, —N($C_1C_4$ alkyl)—, N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trichloromethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, phenyl optionally substituted with 1–3 ($C_1$–$C_4$) alkyl, —$CO_2H$, —CN, —$CONHR^1$, —$NH_2$, $C_1$–$C_4$ alkylamino, $C_1$–$C_4$ dialkylamino, —$NHSO_2R^1$, —$NHCOR^1$, —$NO_2$;

c) a six-membered saturated, unsaturated or partially unsaturated heterocycle containing up to two heteroatoms selected from the group consisting of —O—, —NH—, —N($C_1C_4$ alkyl)—, N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trichloromethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) allkyl, phenyl optionally substituted with 1–3 ($C_1$–$C_4$) alkyl, —$CO_2H$, —CN, —$CONHR^1$, —$NH_2$, $C_1$–$C_4$ alkylamino, $C_1$–$C_4$ dialkylamino, —$NHSO_2R^1$, —$NHCOR^1$, —$NO_2$;

d) a seven-membered saturated, unsaturated or partially unsaturated heterocycle containing up to two heteroatoms selected from the group consisting of —O—, —NH—, —N($C_1C_4$ alkyl)—, N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trichloromethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) allkyl, phenyl optionally substituted with 1–3 ($C_1$–$C_4$) alkyl, —$CO_2H$, —CN, —$CONHR^1$, —$NH_2$, $C_1$–$C_4$ alkylamino, $C_1$–$C_4$ dialkylamino, —$NHSO_2R^1$, —$NHCOR^1$, —$NO_2$;

e) a bicyclic heterocyclic containing from 6–12 carbon atoms either bridged or fused and containing up to two heteroatoms selected from the group consisting of —O—, —NH—, —N($C_1C_4$ alkyl)—, N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trichloromethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) allkyl, phenyl optionally substituted with 1–3 ($C_1$–$C_4$) alkyl, —$CO_2H$, —CN, —$CONHR^1$, —$NH_2$, $C_1$–$C_4$ alkylamino, $C_1$–$C_4$ dialkylamino, —$NHSO_2R^1$, —$NHCOR^1$, —$NO_2$;

and the pharmaceutically acceptable salts thereof.

Within the scope of the compounds described above are preferred compounds of Formulas I or II wherein $R_1$, $R_2$, $R_3$, $R_4$, $R_5$, $R_6$, X, n', and n are as defined above and Y is selected from saturated five-, six- or seven-membered heterocyclic or bicyclic structures with the heteroatoms and substituents described in groups b) through e), above. Among the further preferred Y groups of this subset are those shown below, each unsubstituted or optionally substituted by the substituents described above.

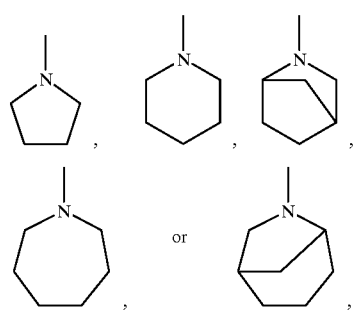

The more preferred compounds of this invention are those having the general structures I, or II, above, wherein:

$R_1$ is selected from H, OH or the $C_1$–$C_4$ esters or alkyl ethers thereof, halogen;

$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;

Y is the moiety

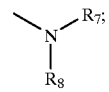

$R_7$ and $R_8$ are selected independently from H, $C_1$–$C_6$ alkyl, or combined by —($CH_2$)p—, wherein p is an integer of from 2 to 6, so as to form a ring, the ring being optionally substituted by up to three substituents selected from the group of hydrogen, hydroxy, halo, $C_1$–$C_4$ alkyl, trichloromethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$) allkyl, —$CO_2H$, —CN, —$CONH(C_1$–$C_4$), —$NH_3$, $C_1$–$C_4$ alkylamino, $C_1$–$C_4$ dialkylamino, —$NHSO_2$ ($C_1$–$C_4$), —$NHCO(C_1$–$C_4$), and —$NO_3$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneimine or heptamethyleneimine rings.

The most preferred compounds of the present invention are those having the structural formulas I or II, above, wherein $R_1$ is OH; $R_2$–$R_6$ are as defined above; and Y is the moiety

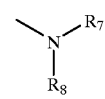

and $R_7$ and $R_8$ are concatenated together as —($CH_2$)$_r$—, wherein r is an integer of from 4 to 6, to form a ring optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$) allkyl, —$CO_2H$, —CN, —$CONH(C_1$–$C_4$), —$NH_3$, $C_1$–$C_4$ alkylamino, $C_1$–$C_4$ dialkylamino, —$NHSO_2$ ($C_1$–$C_4$), —$NHCO(C_1$–$C_4$), and —$NO_2$;

and the pharmaceutically acceptable salts thereof.

Also included within the subsets of compounds of this invention are compounds of the general formulas:

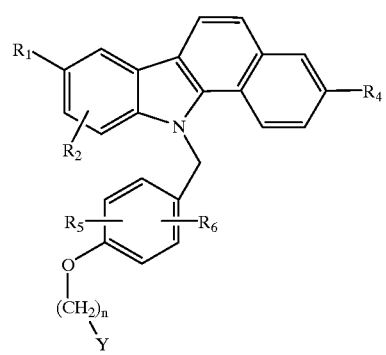

5

-continued or

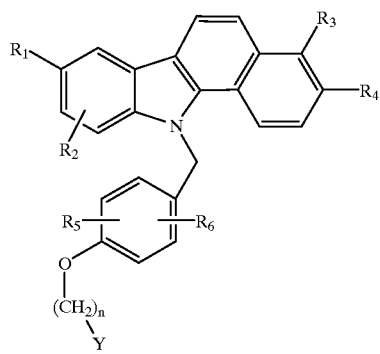

wherein $R_1, R_2, R_3, R_4, R_5, R_6, R_7, R_8, Y, r, n, n'$, and p are as defined in the groups described above.

The invention includes acceptable salt forms formed from the addition reaction with either inorganic or organic acids. Inorganic acids such as hydrochloric acid, hydrobromic acid, hydroiodic acid, sulfuric acid, phosphoric acid, nitric acid are useful as well as organic acids, such as acetic acid, propionic acid, citric acid, maleic acid, maleic acid, tartaric acid, phthalic acid, succinic acid, methanesulfonic acid, toluensulfonic acid, naphthalenesulfonic acid, camphorsulfonic acid, benzenesulfonic acid. It is known that compounds possessing a basic nitrogen can be complexed with many different acids (both protic and not protic) and usually it is preferred to administer a compound of this invention in the form of an acid addition salt. Additionally, this invention includes quaternary ammonium salts of the compounds herein, which can be prepared by reacting the nucleophilic amines of the side chain with a suitably reactive alkylating agent such as an alkyl halide or benzyl halide.

Methods

The synthesis of the compounds described in this invention is accomplished by simply heating either an indanone or a tetralone with the appropriately substituted phenylhydrazine and a protic acid to yield the desired hydrazone which is then cyclized upon further heating with a Lewis acid (e.g. $ZnCl_2$). The indenoindole or benzo[a]carbazole can then be alkylated by deprotonation with a suitably strong base (e.g. NaH) and then treated with the desired side chain. The general scheme for the synthesis of these compounds is illustrated in scheme 1. This concept is illustrated in scheme 2 specifically for the synthesis of compound 6. The synthesis of the side chain 11 is shown in scheme 3.

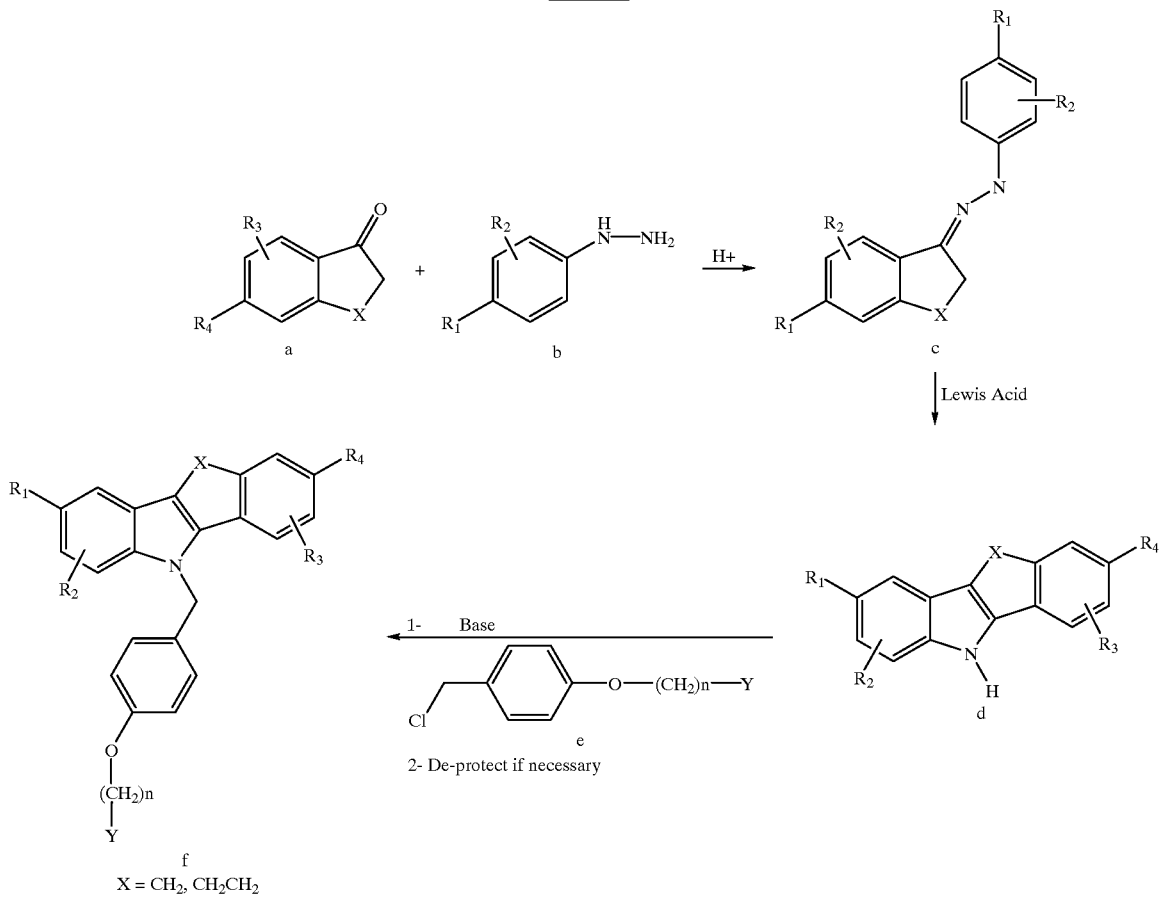

Scheme 1

Scheme 2
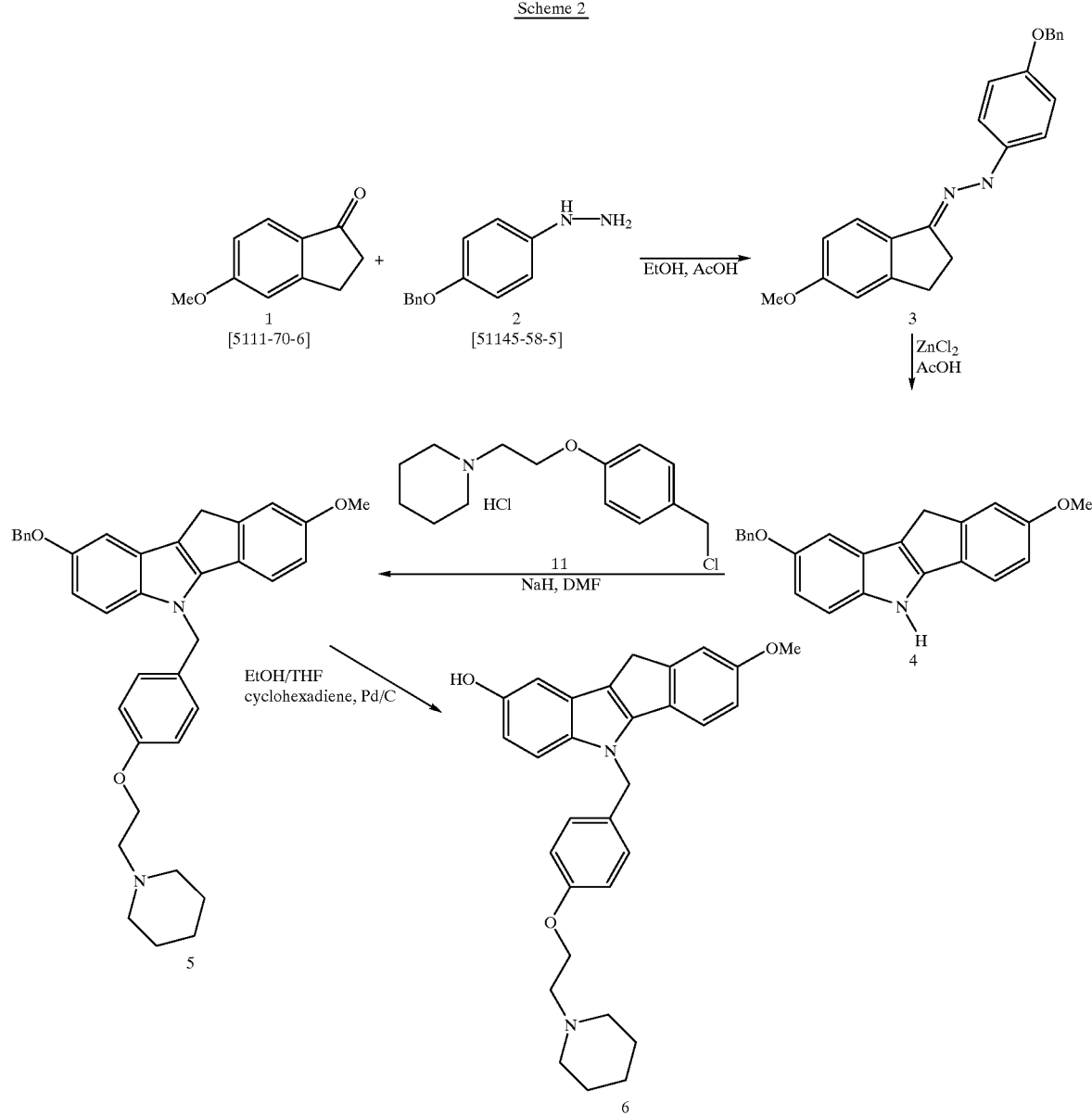
Scheme 3
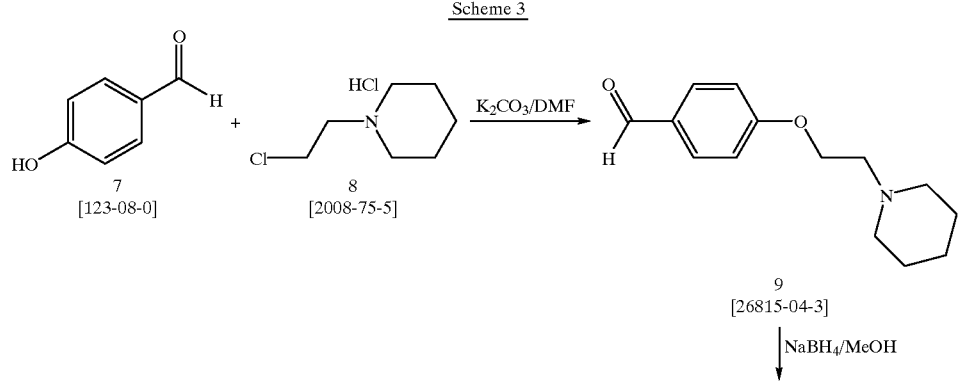

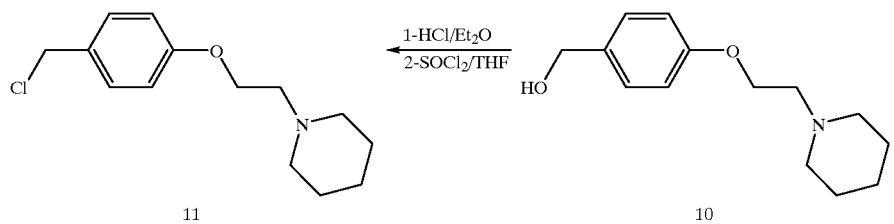

The synthesis of benzo[a]carbazoles (19 through 22) are shown in scheme 4. The tetralone hydrazone 14 is formed from the condensation reaction between 6-methoxy-1-tetralone 12 ([1078-19-9] Aldrich Chemical Company) and 4-benzyloxyphenylhydrazine 13 [51145-58-5] in the presence of ethanol and catalytic acetic acid. The hydrazone is then cyclized in the presence of zinc chloride in acetic acid to give the N-unsubstituted benzo[a]carbazole 15. The benzo[a]carbazole can then be alkylated in the same fashion as shown in scheme 1 or 2, or alternatively, as shown in scheme 4, with 4-(2-chloroethoxy)-benzylbromide 17 as the alkylating agent. The chloride is displaced with piperidine or hexamethyleneimine for the examples given, using DMF as the solvent and potassium iodide to facilitate the reaction. The substituted compounds, 19 and 20, are then hydrogenated with cyclohexadiene and a palladium/carbon catalyst to yield compounds 21 and 22.

Scheme 4

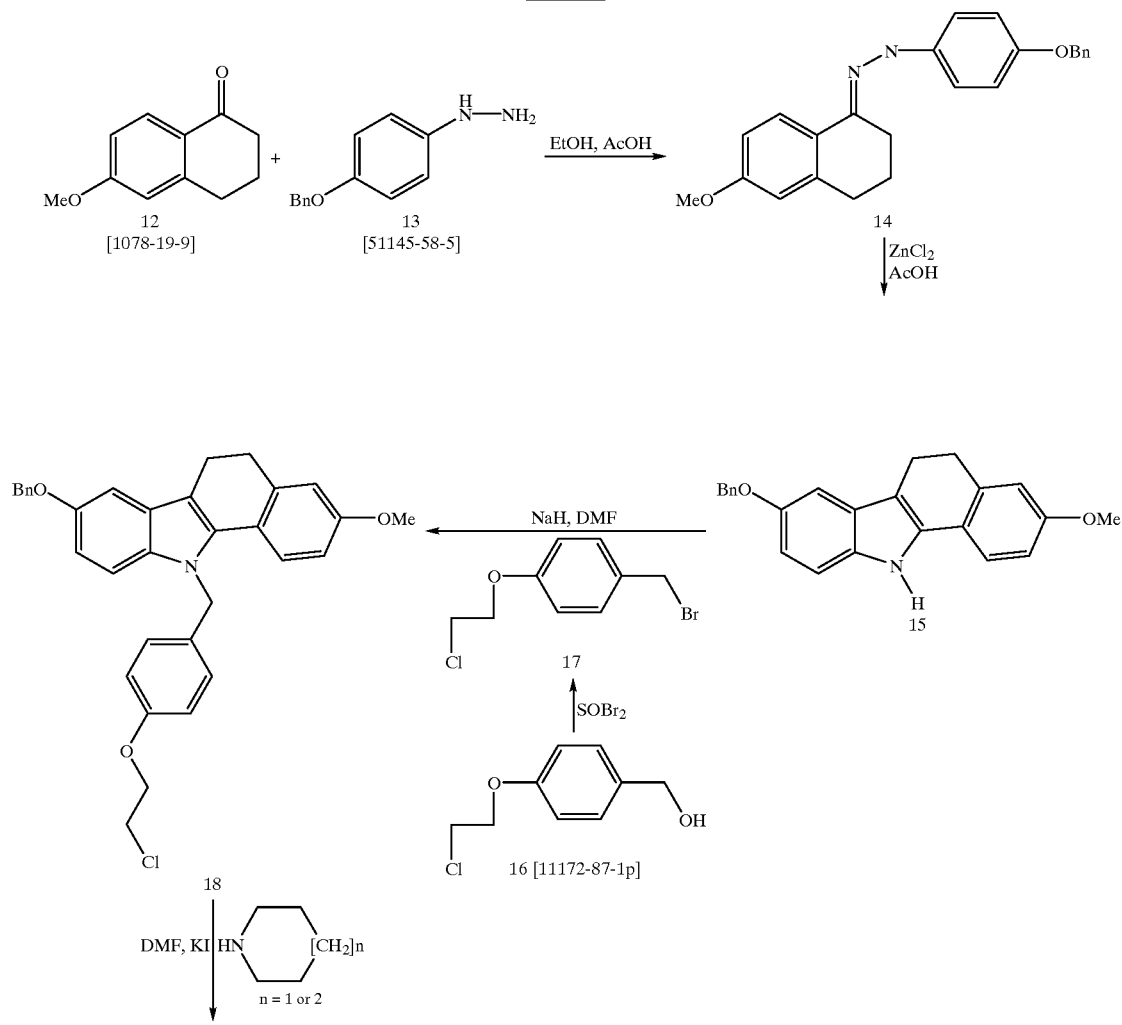

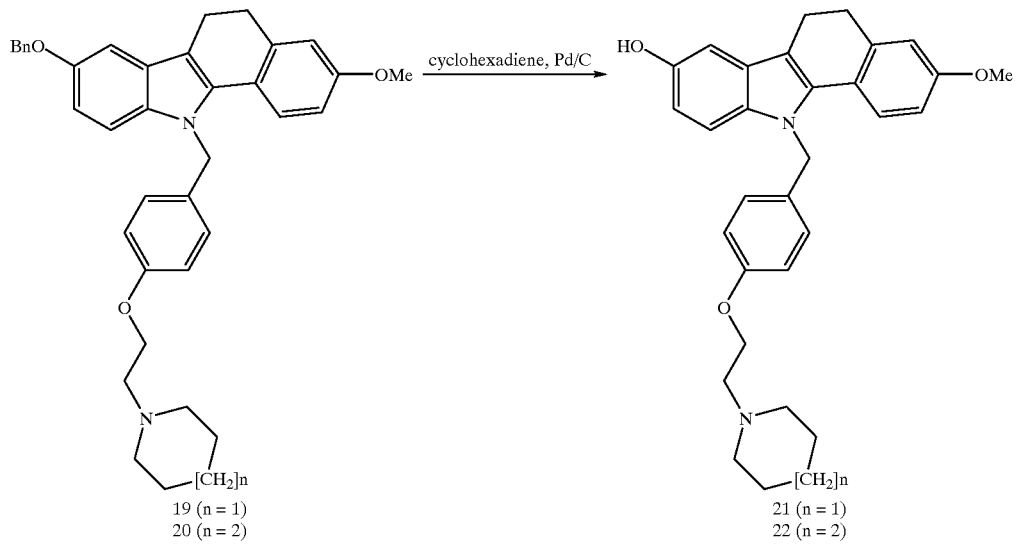

19 (n = 1)
20 (n = 2)

21 (n = 1)
22 (n = 2)

The compounds of the invention are partial estrogen agonists and display high affinity for the estrogen receptor. Unlike many estrogens, these compounds would not be expected to cause substantial increases in uterine wet weight which is evidenced by their low agonism in the infection luciferase assay. Additionally, these compounds compete with estrogen for the estrogen receptor and thus are capable of antagonizing the effects of estrogens in targeted tissues. Due to the tissue selective nature of these compounds, they are useful in treating or preventing in a mammal disease states or syndromes which are caused or associated with an estrogen deficiency or an excess of estrogen.

Mixed estrogen agonists/antagonists are useful for treating or preventing many maladies which result from estrogen excess or deficiency including osteoporosis, prostatic hypertrophy, male pattern baldness, ovarian cancer, infertility, breast cancer, endometrial cancer, cardiovascular disease, contraception, Alzheimer's disease, cognitive decline and other CNS disorders, as well as certain cancers including melanoma, prostrate cancer, cancers of the colon, CNS cancers and uterine cancer, among others. Additionally, these compounds can be used for hormone replacement therapy in post-menopausal women or in other estrogen deficiency states where estrogen supplemention would be beneficial.

The compounds of this invention may also be used in methods of treatment for bone loss, which may result from an imbalance in an individual's formation of new bone tissues and the resorption of older tissues, leading to a net loss of bone. Such bone depletion results in a range of individuals, particularly in post-menopausal women, women who have undergone hysterectomy, those receiving or who have received extended corticosteroid therapies, those experiencing gonadal dysgenesis, and those suffering from Cushing's syndrome. Special needs for bone replacement can also be addressed using these compounds in individuals with bone fractures, defective bone structures, and those receiving bone-related surgeries and/or the implantation of prosthesis. In addition to those problems described above, these compounds can be used in treatments for osteoarthritis, hypocalcemia, hypercalcemia, Paget's disease, osteomalacia, osteohalisteresis, multiple myeloma and other forms of cancer having deleterious effects on bone tissues.

Methods of treating the maladies listed herein are understood to comprise administering to an individual in need of such treatment a pharmaceutically effective amount of one or more of the compounds of this invention or a pharmaceutically acceptable salt thereof. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these compounds will vary according to the malady and the individual being treated and will be subject to the judgement of the medical practitioner involved. It is preferred that the administration of one or more of the compounds herein begin at a low dose and be increased until the desired effects are achieved.

Effective administration of these compounds may be given at an effective dose of from about 0.1 mg/day to about 1,000 mg/day. Preferably, administration will be from about 10 mg/day to about 600 mg/day in a single dose or in two or more divided doses. Such doses may be administered in any manner useful in directing the active compounds herein to the recipient's bloodstream, including orally, parentally (including intravenous, intrapertioneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystaline celluloses, flours, gelatins, gums, etc. Useful table formulation may be made by conventional compression, wet granulations or dry granulating methods and utilize pharmaceutically acceptable diluents, binding agents, lubricants, disintegrants, suspending or stabilizing agents, including, but not limited to, magnesium stearate, steraic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

Experimental

Aldrich Sure Seal™ Solvents, anhydrous without further purification, may be used for the reactions described herein and may be obtained from Aldrich Chemical Company. All reactions were carried out under a nitrogen atmosphere. Chromatography was performed using 230–400 mesh silical gel (Merck Grade 60, Aldrich Chemical Company). Thin layer chromatography was performed with Silica Gel 60 $F_{254}$ plates from EM Science. $^1$H NMR spectra were obtained on a Bruker AM-400 instrument in DMSO and chemical shifts reported in ppm. Melting points were determined on a Thomas-Hoover apparatus and are uncorrected. IR spectra were recorded on a Perkin-Elmer diffraction grating or Perkin-Elmer 784 spectrophotometers. Mass spectra were recorded on a Kratos MS 50 or Finnigan 8230 mass spectrometers. Elemental analyses were obtained with a Perkin-Elmer 2400 elemental analyzer. Compounds for which CHN are reported are within 0.4% of the theoretical value for the formula given. Compound nomenclature was typically arrived at by use of the Beilstein Autonom™ program.

Synthesis of Indenoindoles and Benzocarbazoles

TABLE 1

| Example # | X | Z | R |
|---|---|---|---|
| 3 | CH$_2$ | piperidinyl | Bn |

TABLE 1-continued

| Example # | X | Z | R |
|---|---|---|---|
| 4 | CH$_2$ | piperidinyl | H |
| 11 | —CH$_2$CH$_2$— | piperidinyl | Bn |
| 12 | —CH$_2$CH$_2$— | azepanyl | Bn |
| 13 | —CH$_2$CH$_2$— | piperidinyl | H |
| 14 | —CH$_2$CH$_2$— | azepanyl | H |

EXAMPLE NO. 1

(Intermediate #3 in Scheme 2)

5-Methoxy-1-indanone(4-Benzyloxyphenyl)-hydrazone

A solution of 4-benzyloxyphenylhydrazine [51145-58-5]* (10.0 g, 51 mmole) and 5-methoxy indanone [5111-70-6]** (8g, 55 mmole) and a few drops of AcOH in EtOH (100 ml) was heated to reflux for 1 hr. The reaction was then cooled and a solid precipitated out. The solid was filtered to give 14 g of a tan solid (80%). $^1$H NMR (DMSO) 11.88 (s, 1H), 7.48 (d, 1 H, J=8.4 Hz), 7.43–7.32 (m, 5 H), 7.08 (d, 2 H, J=9.0 Hz), 6.88 (m, 3 H), 6.81 (dd, 1 H, J=8.8 Hz, 2.4 Hz), 5.17 (s, 2 H), 3.75 (s, 3 H), 3.03 (t, 2 H, J=6.6 Hz), 2.73 (t, 2 H, J=6.5 Hz); IR (KBr) 3350 , 1520, 1250 cm$^{-1}$; CHN calc for $C_{23}H_{22}N_2O_2$.

*Prepared by the method given in Miyadera T. and Kosower E. M.:*J.Med.Chem* 15 (1972) 339'340 using 4-benzyloxyaniline (Aldrich Chemical) as the starring material
**Purchased from Aldrich Chemical Company

EXAMPLE NO. 2

(Intermediate #4 in Scheme 2)

2-Methoxy-8-benzyloxy-5,10-dihydro-indeno[1,2-b]indole

A solution of 5-Methoxy-1-indanone(4-Benzyloxyphenyl)-hydrazone (#3 from previous step) (14 g, 41 mmole) and $ZnCl_2$ (14 g, 100 mmol) in AcOH (70 ml) was heated to 110° C. for 30 min. The reaction was then poured into water, extracted with EtOAc. The organic layer was dried with $MgSO_4$ and concentrated. The product was purified by flash chromatography (eluent 20% EtOAc/Hexane) to give a yellow solid. The solid was stirred in ether and filtered to give 2.3 g of an off white solid (17%). Mp=189–193° C.; $^1$H NMR (DMSO) 11.28 (s, 1 H), 7.41 (m, 5 H), 7.32 (m, 2 H), 7.17 (d, 1 H, J=2.4 Hz), 7.10 (d, 1 H, J=2.4 Hz), 6.89 (dd, 1 H, J=8.4 Hz, 2.4 Hz), 6.75 (dd, 1 H, J=8.6 Hz, 2.4 Hz), 5.10 (s, 2 H), 3.78 (s, 3 H), 3.60 (s, 2 H); MS eI m/z 342 (M+).

EXAMPLE NO. 3

(Intermediate No. 5 in Scheme 2)

8-Benzyloxy-2-methoxy-5-[4-(2-piperidin-1-yl-ethoxy)-benzyl]-5,10-dihydro-indeno[1,2]indole Compound #11 (see procedure below) (5.0 g, 23.9 mmol) in DMF (40 mL) was cooled to 0° C. and treated with NaH (60% dispersion in mineral oil, 1.15 g, 28.8 mmol) and stirred for 15 minutes. The resulting solution was treated with the indenoindole #4 (4.0 g, 11.7 mmol) followed by an additional equivalent of NaH (60% dispersion in mineral oil, 0.47 g, 11.7 mmol). The reaction was allowed to come to room temperature (rt) and stirred for 2 hours. The reaction mixture was poured into water and extracted with ethyl acetate, dried over magnesium sulfate and concentrated. The concentrate was chromatographed on silica gel (ethyl acetate/hexanes, 7:3) then with 100% ethyl acetate which yielded a brown solid which was triturated with methanol to yield 3.2 g of an off-white solid: Mp=102–105° C.; $^1$H NMR (DMSO) 7.52 (d, 1 H, J=8.4 Hz), 7.43 (m, 5 H), 7.36 (m, 1 H), 7.18 (d, 1 H, J=2.2 Hz), 7.13 (d, 1 H, J=2.4 Hz), 7.04 (d, 2 H, J=8.6 Hz), 6.85 (dd, 1 H, J=8.3 Hz, 2.4 Hz), 6.80 (m, 3 H), 5.58 (s, 2 H), 5.10 (s, 2 H), 3.93 (t, 2 H, J=5.9 Hz), 3.77 (s, 3 H), 3.64 (s, 2H), 2.55 (t, 2 H, J=5.9 Hz), 2.34 (m, 4H), 1.42 (m, 4 H), 1.33 (m, 2 H); IR (KBr) 2950, 1460, 1250 $cm^{-1}$; MS eI m/z 559 (M+).

EXAMPLE NO. 4

(Product No. 6 in Scheme 2)

2-Methoxy-5-[4-(2-piperidin-1-yl-ethoxy)-benzyl]-5,10-dihydro-indeno[1,2-b]indol-8ol A solution consisting of indenoindole #5, 1.6 g 10% Pd/C, and cyclohexadiene (8 mL) and THF/EtOH (approximately 1:1) was stirred at rt for 18 hours after which time the reaction mixture was filtered through celite, concentrated and triturated with methanol to yield 2.2 g of a white solid: Mp=144–146° C.; $^1$H NMR (DMSO) 8.74 (s, 1 H), 7.48 (d, 1 H, J=8.4 Hz), 7.29 (d, 1 H, J=8.8 Hz), 7.16 (d, 1 H, J=2.2 Hz), 7.04 (d, 2 H, J=8.8 Hz), 6.82 (m, 4 H), 6.55 (dd, 1 H, J=8.8 Hz, 2.2 Hz), 5.53 (s, 2 H), 3.93 (t, 2 H, J=6.0 Hz), 3.76 (s, 3 H), 3.60 (s, 2 H), 2.55 (t, 2 H, J=5.9 Hz), 2.34 (m, 4 H), 1.43 (m, 4 H), 1.33 (m, 2 H); IR (KBr) 3400, 2910, 1460, 1250 $cm^{-1}$; MS eI m/z 469 (M+); CHN calc for $C_{30}N_{32}N_2O_3$+0.5 $H_2O$+0.4 ethanol.

EXAMPLE NO. 5

(Intermediate No. 9 in Scheme 3)

4-(2-piperidin-ethoxy)-benzyl aldehyde

To a well-stirred slurred of p-hydroxybenzaldehyde [123-08-0] (83.5 g, 0.68 mol) and $K_2CO_3$ (224 g, 1.6 mol) in DMF (1 L), 1-(2-chloroethyl)piperidine [2008-75-5] (120 g, 0.65 mol) was added. The reaction mixture was refluxed for 2 hr with vigorous mechanical stirring. After 2 h, the reaction mixture was filtered through celite, diluted with EtOAc (2L), and washed with water (3×500 mL). The organic layer was concentrated to yield 147 g of aldehyde #9 [138351-15-2] as a yellow oil: $^1$H NMR ($CDCl_3$) 9.87 (s, 1 H), 7.81 (d, 2 H, J=8.7 Hz), 7.02 (d, 2 H, J=8.7 Hz), 4.14 (t, 2 H, J=6.1 Hz), 2.98 (t, 2 H, J=6.1 Hz), 2.78 (m, 4 H), 1.66–1.61 (m, 8 H).

EXAMPLE NO. 6

(Intermediate No. 10 in Scheme 3)

4-(2-piperidin-ethoxy)-benzyl alcohol

To a stirred solution of the aldehyde #9 (115 g, 0.49 mol) in MeOH (0.36 L) at 0° C., $NaBH_4$ (9.44 g, 0.25 mol) was added portionwise. The reaction was allowed to stir for 30 minutes and poured into water and extracted with $CH_2Cl_2$ and then dried over $MgSO_4$. The solution was concentrated to give 91.6 g of an oil which crystallized upon seeding: $^1$H NMR ($CDCl_3$) 7.23 (d, 2 H, J=8.5 Hz), 6.80 (d, 2 H, J=8.5 Hz), 4.56 (s, 2 H), 3.99 (t, 2 H, J=6.1 Hz), 2.69 (t, 2 H, J=6.1 Hz), 2.47 (m, 4 H), 1.60–1.25 (m, 6 H); $^{13}$C NMR (DMSO) 158.2, 135.3, 128.7, 114.8, 66.4, 63.4, 58.3, 55.3, 26.4, 24.8.

EXAMPLE NO. 7

(Intermediate No. 11 in Scheme 3)

(4-Chloromethyl-phenoxy)-ethyl-piperidin hydrochloride

A solution of the alcohol #10 (61.3 g, 0.26 mol) in THF (0.5 L) was cooled to 0° C. and gaseous HCL bubbled through. The bubbling was continued until no more thickening was observed. The ice bath used to cool the reaction was removed and $SOCl_2$ (29 mL, 0.39 mol) added and then the mixture heated at 50° C. until the mixture became clear. The reaction mixture was cooled to –3° C. and stirred for 30 minutes. A white solid precipitated out and was filtered and dried to give 72 g of the chloride #11: $^1$H NMR (DMSO) 11.0 (br s, 1 H), 7.39 (d, 2 H, J=8.5 Hz), 6.99 (d, 2 H, J=8.5 Hz), 4.74 (s, 2 H), 4.46 (m, 2 H), 3.45 (m, 4 H), 2.69 (m, 2 H), 1.90–1.20 (m, 6 H).

EXAMPLE NO. 8

(Intermediate No. 14 in Scheme 4)

5-Methoxy-1-tetralone-(4-Benzyloxyphenyl)-hydrazone

A solution of 6-methoxy-1-tetyralone [1078-19-9]* (14.8 g, 84 mmol) and 4-benzyloxyphenyl hydrazine [5111-70-6]** (15.0 g, 70 mmol) and a few drops of AcOH in EtOH was heated to reflux for 1 hr. The reaction was then cooled and a solid precipitated out. The solid was filtered to give 21.5 g of #14: Mp=86–91° C.; $^1$H NMR (DMSO) 8.8 (s, 1 H), 8.00–6.50 (m, 12 H), 5.00 (s, 2 H), 3.82 (s, 3 H), 2.80–2.65 (m, 4 H), 1.90 (t, 2 H, J=6.0 Hz).

*Aldrich Chemical Company
**Prepared by the method given in Miyadera T. and Kosower E. M.:*J.Med.Chem* 15 (1972) 339–340 using 4-benzyloxyaniline (Aldrich Chemical) as the starting material.

EXAMPLE NO. 8(b)

(Intermediate No. 15 in Scheme 4)

3-Methoxy-8-benzyloxy-5,11-dihydro-6H-benzol[a]carbazole

A flask containing hydrazone #14 (23 g, 61.7 mmol), $ZnCl_2$ (21.0 g, 154.4 mmol), and 100 mL AcOH was heated to 95° C. for 10 minutes. The reaction was allowed to come to rt and the product precipitated out of the reaction mixture. The product was washed with ether and filtered yielding 21 g of the product #15 as a tan solid: Mp=182–185° C.; $^1$H NMR (DMSO) 11.19 (s, 1 H), 7.59–7.36 (m, 6 H), 7.26 (d, 1 H, J=8.7 Hz), 7.08 (d, 1 H, J=2.3 Hz), 6.94–6.87 (m, 2 H), 6.79 (dd, 1 H, J=8.7 Hz, 2.4 Hz), 5.14 (s, 2 H), 3.81 (s, 3 H), 2.99 (t, 2 H, J=7.1 Hz), 2.86 (t, 2 H, J=6.1 Hz).

EXAMPLE NO. 9

(Intermediate No. 17 in Scheme 4)

4-(2-Chloroethoxy)-benzylbromide 4-(2-Chloroethoxy)benzyl alcohol #16 [11172-87-1p] (6.4 g, 34.3 mmol) in dioxane (100 mL) at 0° C. was added slowly thionylbromide (7.13 g, 34.3 mmol). The reaction was done at 0° C. after 5 min. The reaction mixture was diluted with ether (200 mL) and washed with $H_2O$ (1×30 mL) then $NaHCO_3$ (2×25 mL), and brine (30 mL). The organic extract was dried over $MgSO_4$ and concentrated. The crude product was purified by silica gel chromatography (EtOAC/hexanes; 1:6) to yield 5.0 g (58%) of the desired product #17 as a white solid: Mp=64–66° C.; $^1$H NMR (DMSO) 7.37 (d, 2 H, J=8.8 Hz), 6.93 (d, 2 H, J=8.8 Hz), 4.68 (s, 2 H), 4.24 (t, 2 H, J=5.0 Hz), 3.93 (t, 2 H, J=5.3 Hz); MS eI m/z 248 (M+).

EXAMPLE NO. 10

(Intermediate No. 18 in Scheme 4)

11-[4-(2-Chloroethoxy)-benzyl]-8-benzyloxy-3-methoxy-5,11-dihydro-6H-benzo[a]carbazole Benzo[a]carbazole #15 (10 g, 28.1 mmol) in DMF was cooled to 0° C. and treated with NaH (1.66 g, 41.5 mmol) and stirred for 10 minutes. This solution was then added to a solution of 4-(2-Chloroethoxy)benzylbromide #17 (11.2 g, 45.0 mmol) in DMF and the reaction was stirred at 0° C. for 5 minutes and then allowed to stir at rt for 20 minutes. The reaction was worked up by quenching with water and extracting with ethyl acetate. The ethyl acetate was washed with brine and dried over $MgSO_4$. The reaction mixture was concentrated to leave 15 g of the product as a crude oil which was used as is for the next reaction: $^1$H NMR (DMSO) 7.52–6.82 (m, 13 H), 6.80 (dd, 1 H, J=8.4 Hz, 2.6 Hz), 6.75 (dd, 1 H, 8.8 Hz, 2.4 Hz), 5.56 (s, 2 H), 5.11 (s, 2 H), 4.20 (t, 2 H, J=6.0 Hz), 3.90 (t, 2 H, J=6.2 Hz), 3.73 (s, 3 H), 2.92–2.75 (m, 4 H).

EXAMPLE NO. 11

Compound No. 19 in Scheme 4

3-Methoxy-8-benzyloxy-11-[4-(2-piperidin-1-yl-ethoxy)-benzyl]-5,11-dihydro-6H-benzo[a]carbazole Intermediate #18, 11-[4-(2-Chloroethoxy)-benzyl]-8-benzyloxy-3-methoxy-5,11-dihydro-6H-benzo[a]carbazole, (6 g, 11.5 mmol) in DMF was treated with KI (2.5 g, 15.0 mmol) and piperidine (12 mL) and heated to 65° C. for 18 hours. The reaction was worked up by pouring the crude reaction mixture into water and extracting with ethyl acetate. The ethyl acetate layer was washed with $NaHCO_3$ aq., brine and dried over $MgSO_4$. The resultant was chromatographed on silica gel using $CH_2Cl_2$ (100%), $CH_2Cl_2$:MeOH (98:2), $CH_2Cl_2$:MeOH (96:4) as the eluting solvents. The product (3.2 g) was isolated as an oil: $^1$H NMR (DMSO) 7.52–7.12 (m, 8 H), 6.98–6.82 (m, 5 H), 6.80 (dd, 1 H, J=8.4 Hz, 2.6 Hz), 6.73 (dd, 1 H, J=8.8 Hz, 2.4 Hz), 5.56 (s, 2 H), 5.11 (s, 2 H), 3.98 (t, 2 H, J=6.0 Hz), 3.70 (s, 3 H), 2.85–2.78 (m, 2 H), 2.75 (s, 2 H), 2.60 (t, 2 H, J=6.5 Hz), 2.42–2.38 (m, 4 H), 1.70–1.58 (m, 4 H), 1.58–1.35 (m, 2 H).

EXAMPLE NO. 12

Compound No. 20 in Scheme 4

11-[4-(2-Azepan-1-yl-ethoxy)-benzyl]-8-benzyloxy-3-methoxy-5,11-dihydro-6H-benzo[a]carbazole

20 was prepared analogously to #19 except that the amine used was hexamethyleneimine. The product was isolated as an oil: $^1$H NMR (DMSO) 7.52–7.12 (m, 8 H), 6.98–6.82 (m, 5 H), 6.80 (dd, 1 H, J=8.4 Hz, 2.6 Hz), 6.73 (dd, 1 H, J=8.8 Hz, 2.4 Hz), 5.56 (s, 2 H), 5.10 (s, 2 H), 3.97 (t, 2 H, J=6.0 Hz), 3.73 (s, 3 H), 2.85–2.70 (m, 6 H), 2.68–2.62 (m, 4 H), 1.70–1.43 (m, 8 H).

EXAMPLE NO. 13

Compound No. 21 in Scheme 4

3-Methoxy-11-[4-(2-piperidin-1-yl-ethoxy)-benzyl]-5,11-dihydro-6H-benzo[a]carbazol-8-ol Compound #19 (3.2 g) was dissolved in THF/EtOH (30 mL, 1:1) and treated with 10% Pd/C (1.2 g) and cyclohexadiene (8 mL). The reaction was stirred at rt for 3 h and then filtered through celite and concentrated. The crude product was precipitated from methanol to yield #21 (1.3 g) as a white solid: Mp=141–143° C., $^1$H NMR (DMSO) 8.75 (s, 1 H), 7.27 (d, 1 H, J=8.5 Hz), 7.09 (d, 1 H, J=8.5 Hz), 7.00–6.90 (m, 3 H), 6.84 (d, 2 H, J=8.8 Hz), 6.80 (d, 1 H, J=2.4 Hz), 6.70 (dd, 1 H, J=8.4 Hz, 2.6 Hz), 6.58 (dd, 1 H, 8.8 Hz, 2.4 Hz), 5.45 (s, 2 H), 3.98 (t, 2 H, J=6.0 Hz), 3.70 (s, 3 H), 2.89 (t, 2 H, J=6.6 Hz), 2.75 (t, 2 H, J=6.5 Hz), 2.60 (t, 2 H, J=6.5 Hz), 2.40–2.30 (m, 4 H), 1.53–1.40 (m, 4 H), 1.39–1.30 (m, 2 H); MS [M+H] observed at m/z=483; CHN calcd for $C_{31}H_{34}N_2O_3$+0.60 $H_2O$.

EXAMPLE NO. 14

Compound No. 22 in Scheme 4

11-[4-(2-Azepan-1-yl-ethoxy)-benzyl]-3-methoxy-5,11-dihydro-6H-benzo[a]carbazol-8-ol Reaction was performed analogously to that described for the synthesis of example #21: Mp=115–118° C.; $^1$H NMR (DMSO) 8.74 (s, 1 H), 7.27 (d, 1 H, J=8.5 Hz), 7.08 (d, 1 H, J=8.5 Hz), 7.0–6.90 (m, 3 H), 6.84 (d, 2 H, J=8.8 Hz), 6.80 (d, 1 H, J=2.4 Hz), 6.71 (dd, 1 H, J=8.5 Hz, 2.6 Hz), 6.58 (dd, 1 H, J=8.8 Hz, 2.4 Hz), 5.48 (s, 2 H), 3.94 (t, 2 H, J=6.0 Hz), 3.72 (s, 3 H), 2.87 (t, 2 H, J=6.6 Hz), 2.80–2.73 (m, 4 H), 2.64–2.60 (m, 4 H, J=4.4 Hz), 1.60–1.45 (m, 8 H); IR (KBr) 3400, 2900, 1500, 1250; MS (–) FAB m/z 495 (M–H)$^-$; CHN calcd for $C_{32}H_{36}N_2O_3$+0.33 $CH_3OH$.

Scheme 5

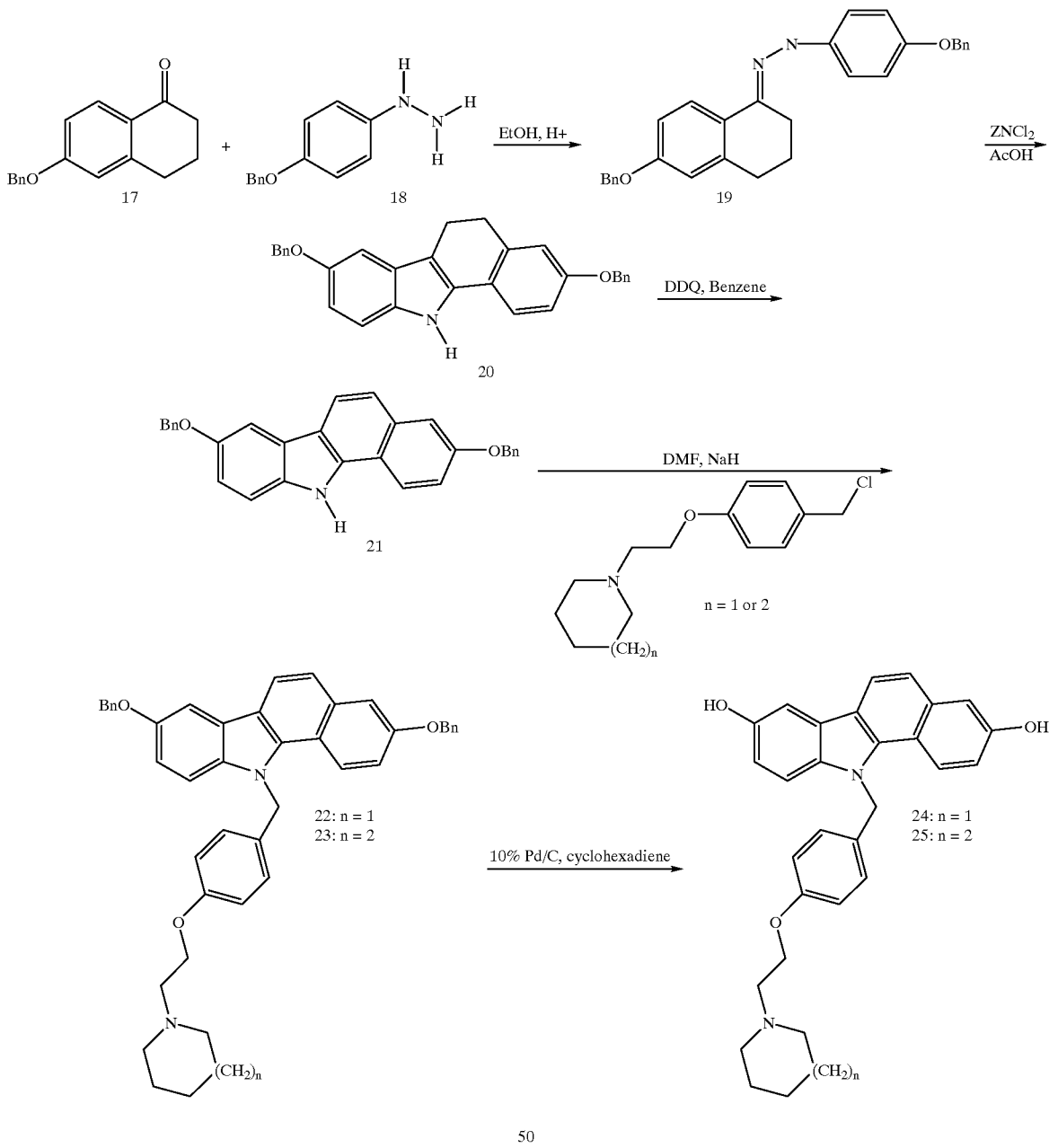

The benzocarbazoles of Scheme 5 were prepared analogously to the dihydro compounds, however, the added step of oxidizing the dihydrocarbazole intermediate 20 using 2,3-Dichloro-5,6-dicyanobenzoquinone (DDQ) was inserted into the sequence.

EXAMPLE NO. 15

Hydrazone 19 in Scheme 5

A solution consisting of 4-benzyloxyphenylhydrazide 18 (8 g, 37.3 mmol), 4-bezyloxytetralone 17 (11.3 g, 44.8 mmol), AcOH (5 drops) in EtOH (100 mL) was heated to reflux for 3 hours during which time all of the reactants went into solution. The reaction was cooled to 0° C. and the product precipitated out and was filtered out. The product 20 (9.5 g) was isolated as a white solid: mp 102–104° C. We found that the product was best used immediately because the products sitting out at room temperature results in discoloration.

EXAMPLE NO. 16

Dihydrobenzocarbazole 20 in Scheme 5

3,8-Bis-benzyloxy-5,11-dihydro-6H-benzo[a]carbazole

The hydrazone 19 (7.5 g, 16.7 mmol) was dissolved in AcOH (50 mL) and treated with ZnCl$_2$ (5.7 g, 42 mmol) and then heated at 105° C. for 15 minutes during which time everything went into solution. The reaction was allowed to room temperature and worked up by partitioning the reaction mixture between Et$_2$O and H$_2$O. The product 20, which was soluble in neither layer was isolated by filtering the biphasic mixture. The product was isolated as a white solid (5.6 g): mp 177–180° C.; MS APCI 430 (M–H).

EXAMPLE NO. 17

Benzocarbazole 5 in Scheme 5

3,8-Bis-benzyloxy-11H-benzo[a]carbazole

The dihydrocarbazole 20 (5.1 g, 11.9 mmol) in benzene (50 mL) was treated with DDQ (3.2 g, 14 mmol) and heated at reflux for 3 hours. The crude reaction mixture was partitioned between EtOAc and $H_2O$ and the product, which was soluble in neither layer, was filtered off. The crude precipitate thus filtered was triturated with $Et_2O$ to yield the desired material 21 as a light grey solid (3.4 g): mp 244–248° C.; MS eI 429.

EXAMPLE NO. 18

Alkylated Benzocarbazole 22 in Scheme 5

3,8-Bis-benzyloxy-11-[4-(2-piperdin-1-yl-ethoxy)-benzyl]-11H-benzo[a]carbazole

The benzocarbazole 21 (1.2 g, 2.8 mmol) was put in DMF (30 mL) (starting material appears insoluble in this solvent) and cooled to 0° C. and treated with NaH (60% dispersion in mineral oil, 300 mg, 7.8 mmol) and stirred at 0° C. for 15 minutes. The piperidinoethoxy benzyl chloride side chain was added (0.97 g, 3.3 mmol) and the reaction stirred an additional 15 minutes at 0° C. followed by 1 h at rt. The reaction was partitioned between EtOAc and $H_2O$ and the product, which was soluble in neither layer, was filtered off. The product was triturated with $Et_2O$ to yield the desired product 6 (1.3 g) as a white solid: mp=171–173° C.; MS (+) ESI 647 (M+H).

EXAMPLE NO. 19

Alkylated Benzocarbazole 23 in Scheme 5

11-[4-(2-Azepan-1-yl-ethoxy)-benzyl]-3,8-bis-benzyloxy-11H-benzo[a]carbazole

Benzocarbazole 23 was prepared analogously to benzocarbazole 22: mp 175–177° C.; MS ESI (+) 661 (M+H).

EXAMPLE NO. 20

Benzocarbazole 24 in Scheme 5

11-[4-(2-Piperidin-1-yl-ethoxy)-benzyl]-11H-benzo[a]carbazole-3,8-diol

A solution consisting of protected benzocarbazole 22 (1.15 g) in THF/EtOH (75:25) was treated with cyclohexadiene (4.5 mL) and 10% Pd/C (0.45 g) and allowed to stir at room temperature overnight. The solution was filtered through Celite and chromatographed on silica gel (10% MeOH/$CH_2Cl_2$) to yield the product which was triturated with $Et_2O$ to render the product as a light grey solid: mp 249–251° C.; $^1$H NMR (DMSO) δ 9.68 (s, 1 H), 9.05 (s, 1 H), 8.21 (d, 1 H, J=9.2 Hz), 8.04 (d, 1 H, J=8.5 Hz), 7.48 (d, 1 H, J=2.2 Hz), 7.46–7.40 (m, 2 H), 7.26 (d, 1 H, J=2.4 Hz), 6.70–6.96 (m, 3 H), 6.89 (dd, 1 H, J=8.7 Hz, 2.2 Hz), 6.83 (d, 2 H, J=8.6 Hz), 5.92 (s, 2 H), 3.95 (t, 2 H, J=5.8 Hz), 2.63–2.55 (m, 2 H), 2.42–2.33 (m, 4 H), 1.50–1.42 (m, 4 H), 1.38–1.29 (m, 2 H); MS ESI (+) 467 (M+H).

EXAMPLE NO. 21

Benzocarbazole 25 in Scheme 5

11-[4-(2-Azepan-1-yl-ethoxy)-benzyl]-11H-benzo[a]carbazole 3,8-diol

Benzocarbazole 25 was prepared analogously to benzocarbazole 23: mp 204–206° C.; $^1$H NMR (DMSO) δ 9.7 (br s, 1 H), 9.1 (br s, 1 H), 8.21 (d, 1 H, J=9.2 Hz), 8.04 (d, 1 H, J=8.5 Hz), 7.48 (d, 1 H, J=2.2 Hz), 7.46–7.40 (m, 2 H), 7.26 (d, 1 H, J=2.39 Hz), 7.02–6.97 (m, 3 H), 6.88 (dd, 1 H, J=8.7 Hz, 2.1 Hz), 6.82 (d, 2 H, J=8.6 Hz), 5.92 (s, 2 H), 3.92 (t, 2 H, J=6.0 Hz), 2.76 (t, 2 H, J=6.0 Hz), 2.65–2.57 (m, 4 H), 1.57–1.48 (m, 8 H); MS ESI (+) 481 (M+H).

BIOLOGICAL DATA

In vitro Estrogen Receptor Binding Assay

Receptor preparation

CHO cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 g to produce a ribosome free cytosol. The cytosol was then frozen and stored at –80° C. Protein concentration of the cytosol was estimated using the BCA assay with reference standard protein.

Binding assay conditions

The competition assay was performed in a 96-well plate (polystyrene*) which binds <2.0% of the total input [$^3$H]-17β-estradiol and each data point was gathered in triplicate. 100 uG/100 uL of the receptor preparation was aliquoted per well. A saturating dose of 2.6 nM [$^3$H]17β-estradiol+ competitor (or buffer) in a 50 uL volume was added in the preliminary competition when 100× and 500× competitor were evaluated, only 0.8 nM [$^3$H] 17β-estradiol was used. The plate was incubated at room temperature for 2.5 h. At the end of this incubation period 150 uL of ice-cold dextran coated charcoal (5% activated charcoal coated with 0.05% 69K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of [$^3$H]17β-estradiol, wells containing radioactivity and cytosol, but not processed with charcoal were included to quantitate amounts of available isotope. Also, wells containing radioactivity but no cytosol were processed with charcoal to estimate unremovable DPM of [$^3$H] 17β-estradiol.

Analysis of results

Counts per minute (CPM) of radioactivity were automatically converted to disintegrated per minute (DPM) by the Beckman LS 7500 Scintillation Counter using a set of quenched standards to generate a H# for each sample. To calculate the % of estradiol binding in the presence of 100 or fold 500 fold competitor the following formula was applied:

((DPM sample–DPM not removed by charcoal/(DPM estradiol–DPM not removed by charcoal))×100%=% of estradiol binding For the generation of $IC_{50}$ curves, % binding is plotted vs compound. $IC_{50}$'s are generated for compounds that show >30% competition at 500× competitor concentration.

TABLE 2

Estrogen Receptor Binding

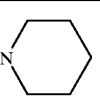

| Example # | X | Z | Receptor Binding IC50's uM |
|---|---|---|---|
| 4 | —CH$_2$— | 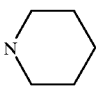 | 0.43 |
| 13 | —CH$_2$CH$_2$— |  | 0.11 |
| 14 | —CH$_2$CH$_2$— | (azepane) | 0.19 |

2× VIT ERE Infection Assay

Cell Maintenance and Treatment

Chinese Hamster Ovary cells (CHO) which had been stably transfected with the human estrogen receptor were maintained in DMEM+10% fetal bovine serum (FBS). 48 h prior to treatment the growth medium was replaced with DMEM lacking phenol red+10% dextran coated charcoal stripped FBS (treatment medium). Cells were plated at a density of 5000 cells/well in 96-well plates containing 200 μL of medium/well.

Calcium Phosphate Transfection

Reporter DNA (Promega plasmid pGL2 containing two tandem copies of the vitellogenin ERE in front of the minimal thymidine kinase promoter driving the luciferase gene) was combined with the B-galactosidase expression plasmid pCH110 (Pharmacia) and carrier DNA (pTZ18U) in the following ratio:

10 uG of reporter DNA
5 uG of pCH110DNA
5 uG of pTZ18U
20 uG of DNA/1 mL of transfection solution The DNA (20 uG) was dissolved in 500 uL of 250 mM sterile CaCl$_2$ and added dropwise to 500 uL of 2× HeBS (0.28 M NaCl, 50 mM HEPES, 1.5 mM Na$_2$HPO$_4$, pH 7.05) and incubated at room temperature for 20 minutes. 20 uL of this mixture was added to each well of cells and remained on the cells for 16 h. At the end of this incubation the precipitate was removed, the cells were washed with media, fresh treatment media was replaced and the cells were treated with either vehicle, 1 nM 17β-estradiol, 1 uM compound or 1 uM compound+1 nM 17β-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed 2× with 125 uL of PBS lacking Mg$^{++}$ and Ca$^{++}$. After removing the PBS, 25 uL of Promega lysis buffer was added to each well and allowed to stand at room temperature for 15 min, followed by 15 min at −80° C. and 15 min at 37° C. 20 uL of lysate was transferred to an opaque 96 well plate for luciferase activity evaluation and the remaining lysate (5 uL) was used for the B-galactosidase activity evaluation (normalize transfection). The luciferan substrate (Promega) was added in 100 uL aliquots to each well automatically by the luminometer and the light produced (relative light units) was read 10 seconds after addition.

Infection Luciferase Assay (Standards)

| Compound | % Activation |
|---|---|
| 17β-estradiol | 100% activity |
| estriol | 38% activity |
| Raloxifene | 0% |

B-Galactosidase Assay

To the remaining 5 uL of lysate 45 uL of PBS was added. Then 50 uL of Promega B-galactosidase 2× assay buffer was added, mixed well and incubated at 37° C. for 1 hour. A plate containing a standard curve (0.1 to 1.5 milliunits in triplicate) was set up for each experimental run. The plates were analyzed on a Molecular Devices spectrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc) file where background RLUs were subtracted. The B-galactosidase values were automatically imported into the file and these values were divided into the RLUs to normalize the data. The mean and standard deviations were determined from a n=8 for each treatment. Compounds activity was compared to 17β-estradiol for each plate. Percentage of activity as compared to 17β-estradiol was calculated using the formula %=((Estradiol-control)/(compound value))×100.

TABLE 3

Infection Luciferase Activity

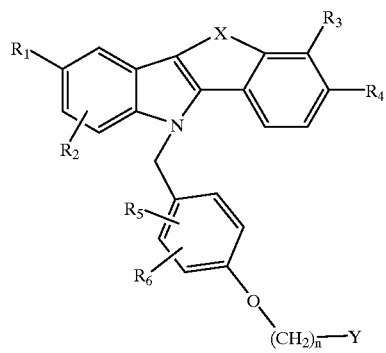

| Example # | X | Z | 1 uM | 1 uM + 17β estradiol |
|---|---|---|---|---|
| 4 | —CH$_2$— |  | -2 | 83 |
| 13 | —CH$_2$CH$_2$— |  | -7 | 1 |
| 14 | —CH$_2$CH$_2$— |  | 1 | 8 |

As can be seen from the data in Table 2, the benzo[a] carbazoles (#21 and #22) bind better to the ER receptor than the indenoindole #6. From the infection luciferase assay data in Table 3, it can be seen that none of the compounds show significant agonistic activity on this promoter. Benzo[a] carbazoles show an ability to antagonize the effects of estradiol to baseline or almost baseline levels.

What is claimed:

1. A compound of formulas I or II:

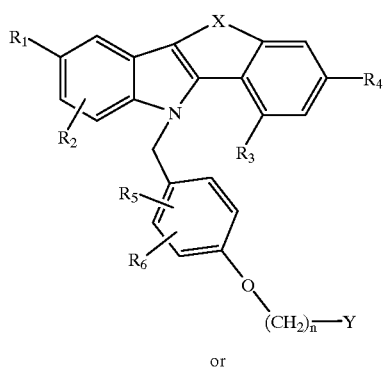

wherein:
R$_1$ is selected from H, OH or an C$_1$–C$_4$ ester or alkyl ether thereof, and halogen;
R$_2$, R$_3$, R$_4$, R$_5$, and R$_6$ are independently selected from H, OH or a C$_1$–C$_4$ ester or alkyl ether thereof, halogen, cyano, C$_1$–C$_6$ alkyl, and trifluoromethyl, with the proviso that, when R$_1$ is H, R$_2$ is not OH;
X is (CH$_2$)$_{n'}$ or —CH═CH—;
n' is 1 or 2;
n is 2–4;
Y is a six-membered saturated, unsaturated or partially unsaturated heterocycle containing up to two heteroatoms selected from the group consisting of —O—, —NH—, —N(C$_1$C$_4$ alkyl)-, —N═, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, and phenyl optionally substituted with 1–3 (C$_1$–C$_4$)alkyl, —CO$_2$H, —CN, CONHR$^1$, —NH$_2$, C$_1$–C$_4$ alkylamino, C$_1$–C$_4$ dialkylamino, —NHSO$_2$R$^1$, —NHCOR$^1$, and —NO$_2$;
or a pharmaceutically acceptable salt thereof.

2. A compound of claim 1 wherein Y is selected from a six-membered saturated heterocycle containing up to two heteroatoms selected from the group consisting of O, —NH—, —N(C$_1$C$_4$ alkyl)-, —N═, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, phenyl optionally substituted with 1–3 (C$_1$–C$_4$)alkyl, —CO$_2$H, —CN, —CONHR$^1$, —NH$_2$, C$_1$–C$_4$ alkylamino, C$_1$–C$_4$ dialkylamino, —NHSO$_2$R$^1$, —NHCOR$^1$, and —NO$_2$;
or a pharmaceutically acceptable salt thereof.

3. A compound of claim 1 wherein:
X is (CH$_2$)$_{n'}$;
n' is 1;
R$_1$ is selected from H, OH or a C$_1$–C$_4$ ester or alkyl ether thereof, and halogen;
R$_2$, R$_3$, R$_4$, R$_5$, and R$_6$ are independently selected from H, OH or a C$_1$–C$_4$ ester or alkyl ether thereof, halogen, cyano, C$_1$–C$_6$ alkyl, and trifluoromethyl, with the proviso that, when R$_1$ is H, R$_2$ is not OH;
Y is a six-membered saturated, unsaturated or partially unsaturated heterocycle containing up to two heteroatoms selected from the group consisting of —O—, —NH—, —N(C₁C₄ alkyl)-, —N=, and —S(O)ₘ—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, and phenyl optionally substituted with 1–3 ($C_1$–$C_4$)alkyl, —CO₂H, —CN, —CONHR¹, —NH₂, $C_1$–$C_4$ alkylamino, $C_1$–$C_4$ dialkylamino, —NHSO₂R¹, —NHCOR¹, and —NO₂;

or a pharmaceutically acceptable salt thereof.

4. A compound of claim 1 wherein:

X is (CH₂)ₙ';

n' is 2;

R₁ is selected from H, OH or the $C_1$–$C_4$ esters or alkyl ethers thereof, halogen;

R₂, R₃, R₄, R₅, and R₆ are independently selected from H, OH or a $C_1$–$C_4$ ester or alkyl ether thereof, halogen, cyano, $C_1$–$C_6$ alkyl, and trifluoromethyl, with the proviso that, when R₁ is H, R₂ is not OH;

Y is a six-membered saturated, unsaturated or partially unsaturated heterocycle containing up to two heteroatoms selected from the group consisting of —O—, —NH—, —N(C₁C₄ alkyl)-, —N—, and —S(O)ₘ—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, and phenyl optionally substituted with 1–3 ($C_1$–$C_4$)alkyl, —CO₂H, —CN, —CONHR¹, —NH₂, $C_1$–$C_4$ alkylamino, $C_1$–$C_4$ dialkylamino, —NHSO₂R¹, —NHCOR¹, and —NO₂;

or a pharmaceutically acceptable salt thereof.

5. A compound of claim 1 wherein:

X is (CH₂)ₙ';

n' is 1;

R₁ is OH;

R₂, R₃, R₄, R₅, and R₆ are independently selected from H, OH or the $C_1$–$C_4$ esters or alkyl ethers thereof, halogen, cyano, $C_1$–$C_6$ alkyl, or trifluoromethyl, with the proviso that, when R₁ is H, R₂ is not OH;

Y is a six-membered saturated heterocycle containing up to two heteroatoms selected from the group consisting of —O—, —NH—, —N(C₁C₄ alkyl)-, —N=, and —S(O)ₘ—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, and phenyl optionally substituted with 1–3 ($C_1$–$C_4$)alkyl, —CO₂H, —CN, —CONHR¹, —NH₂, $C_1$–$C_4$ alkylamino, $C_1$–$C_4$ dialkylamino, —NHSO₂R¹, —NHCOR¹, and —NO₂;

or a pharmaceutically acceptable salt thereof.

6. A compound of claim 1 wherein:

X is (CH₂)ₙ';

n' is 2;

R₁ is OH;

R₂, R₃, R₄, R₅, and R₆ are independently selected from H, OH or the $C_1$–$C_4$ esters or alkyl ethers thereof, halogen, cyano, $C_1$–$C_6$ alkyl, or trifluoromethyl, with the proviso that, when R₁ is H, R₂ is not OH;

Y is a six-membered saturated heterocycle containing up to two heteroatoms selected from the group consisting of —O—, —NH—, —N(C₁C₄ alkyl)-, —N=, and —S(O)ₘ—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, and phenyl optionally substituted with 1–3 ($C_1$–$C_4$)alkyl, —CO₂H, —CN, —CONHR¹, —NH₂, $C_1$–$C_4$ alkylamino, $C_1$–$C_4$ dialkylamino, —NHSO₂R¹, —NHCOR¹, and —NO₂;

or a pharmaceutically acceptable salt thereof.

7. A compound of claim 1 which is 8-Benzyl-2-methoxy-5-[4-(2-piperidin-1-yl-ethoxy)-benzyl]-5,10-dihydro-indeno[1,2-b]indole.

8. A compound of claim 1 which is 2-Methoxy-5-[4-(2-piperidin-1-yl-ethoxy)-benzyl]-5,10-dihydro-indeno[1,2-b]indol-8ol.

9. A compound of claim 1 which is 3-Methoxy-8-benzyloxy 11-[4-(2-piperidin-1 yl ethoxy)-benzyl]-5,11-dihydro-6H-benzo[a]carbazole.

10. A compound of claim 1 which is 3 Methoxy-11-[4-(2-piperidin-1-yl-ethoxy)-benzyl]-5,11-dihydro-6H-benzo[a]carbazol-8-ol.

11. A compound of the formula:

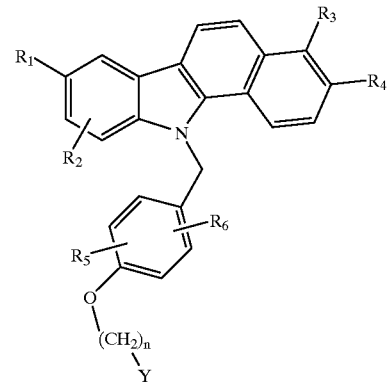

wherein

R₁ is selected from H, OH or the $C_1$–$C_4$ esters or alkyl ethers thereof, halogen;

R₂, R₃, R₄, R₅, and R₆ are independently selected from H, OH or the $C_1$–$C_4$ esters or alkyl ethers thereof, halogen, cyano, $C_1$–$C_6$ alkyl, or trifluoromethyl, with the proviso that, when R₁ is H, R₂ is not OH;

Y is a six-membered saturated, unsaturated or partially unsaturated heterocycle containing up to two heteroatoms selected from the group consisting of O—, —NH—, —N(C₁C₄ alkyl)-, —N—, and —S(O)ₘ—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, and phenyl optionally substituted with 1–3 ($C_1$–$C_4$)alkyl, —CO₂H, —CN, —CONHR¹, —NH₂, $C_1$–$C_4$ alkylamino, $C_1$–$C_4$ dialkylamino, —NHSO₂R¹, NHCOR¹, and —NO₂;

or a pharmaceutically acceptable salt thereof.

12. A compound of claim 11, or a pharmaceutically acceptable salt thereof, wherein Y is the moiety:

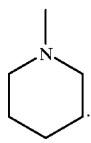

13. A compound of claim 12, which is 11-[4-(2-Piperidin-1-yl-ethoxy)-benzyl]-11H-benzo[a]carbazole-3,8-diol, or a pharmaceutically acceptable salt thereof.

14. A method of treating or preventing bone loss in a mammal, the method comprising administering to a mammal in need thereof an effective amount of a compound of claim 1, or a pharmaceutically acceptable salt thereof.

* * * * *